United States Patent [19]

Chamberlin et al.

[11] Patent Number: 5,340,910
[45] Date of Patent: Aug. 23, 1994

[54] PROCESS FOR PREPARING 1-CYANO-3H-DIBENZ[F,IJ]ISOQUINOLINE-2,7-DIONES AND THEIR USE AS TONERS FOR POLYESTERS

[75] Inventors: Kim S. Chamberlin; Wayne P. Pruett; Max A. Weaver, all of Kingsport; Samuel D. Hilbert, Jonesborough; Donna R. Quillen; Preston K. Salyer, both of Kingsport, all of Tenn.

[73] Assignee: Eastman Chemical Company, Kingsport, Tenn.

[21] Appl. No.: 79,416

[22] Filed: Jun. 21, 1993

Related U.S. Application Data

[62] Division of Ser. No. 883,506, May 15, 1992, Pat. No. 5,252,699.

[51] Int. Cl.$^5$ .................... C08G 69/44; C08G 73/16
[52] U.S. Cl. ...................... 528/289; 524/89; 524/602; 546/26; 546/76
[58] Field of Search ............ 528/289; 546/26, 76; 524/602, 89

[56] References Cited

U.S. PATENT DOCUMENTS

| | | | |
|---|---|---|---|
| 1,891,317 | 12/1932 | Peter | 546/76 |
| 3,459,570 | 8/1969 | Serafin | 106/90 |
| 4,070,581 | 1/1978 | Gibbons et al. | 250/445 |
| 4,403,092 | 9/1983 | Davis et al. | 528/290 |
| 4,420,581 | 12/1983 | McFarlane et al. | 524/431 |
| 4,745,174 | 5/1988 | Pruett et al. | 528/289 |
| 4,790,581 | 12/1988 | Boswell et al. | 292/264 |

*Primary Examiner*—John Kight, III
*Assistant Examiner*—Terressa Mosley
*Attorney, Agent, or Firm*—Bernard J. Graves, Jr.

[57] ABSTRACT

Provided is an improved process for the synthesis of 1-cyano-3H-dibenz[f,ij] isoquinoline-2,7-dione compounds, and process exhibiting improvements in quality of products, safety, fewer environmental concerns and economics when compared to presently known processes. The compounds are useful as colorants for polyesters, and selected compounds and when combined with small quantities of certain red colorants are particularly efficacious as blue toners for polyesters.

14 Claims, No Drawings

PROCESS FOR PREPARING 1-CYANO-3H-DIBENZ[F,IJ]ISOQUINOLINE-2,7-DIONES AND THEIR USE AS TONERS FOR POLYESTERS

This is a divisional application of copending application Ser. No. 07/883,506 filed on May 15, 1992 now U.S. Pat. No. 5,252,699.

FIELD OF THE INVENTION

This invention belongs to the field of organic chemistry. In particular this invention relates to blue/red toners for polyesters.

BACKGROUND OF THE INVENTION

It is known that polyesters prepared by the polycondensation of a dihydric alcohol and a dicarboxylic acid are excellent fiber forming or moldable polymers. Commercially, the most important polyesters are those prepared by the condensation of terephthalic acid or dimethylterephthalate and a polymethylene glycol containing from 2 to 10 carbon atoms, and more particularly ethylene glycol, 1,4-cyclohexanedimethanol, or mixtures thereof. These polyesters are relatively inert and hydrophobic materials which are capable of being formed into filaments which can be drawn to produce textile fibers or plastics of superior strength and pliability.

Unfortunately, native polyester fibers and plastics as manufactured generally have an undesirable yellow appearance. At present, in order to improve the apparent whiteness of polyester fibers or neutral color characteristics of polyester plastics, certain so-called toners are incorporated into the polyester to hide or offset the yellow color. Typically, such toners usually have a visible absorption maximum in the range about 575 nm to 595 nm as measured in acetone.

Cobalt acetate is one of the most widely used toners in the industry to mask the yellow color of polymers. However, cobalt acetate has a number of noteworthy disadvantages. For example, cobalt acetate toned materials tend to be unstable during storage and are particularly susceptible to temperature and humidity, and undergo an undesirable color shift toward yellow. Further, when high cobalt concentrations are needed to mask the yellow color of some polymers there is a tendency to impart a gray color to the polymer.

Another disadvantage in the use of cobalt acetate is the limitations set by various governmental agencies in the level of cobalt deemed allowable in polyester catalyst systems.

Further, cobalt salts tend to lower the resulting polymer's thermal stability and increases acetaldehyde formation in poly(ethylene terephthalate).

Lastly, cobalt has a strong tendency to form insoluble residues in manufacturing process equipment, thereby leading to manufacturing quality control problems.

In U.S. Pat. No. 4,745,174, incorporated herein by reference, certain 1-cyano-3H-dibenz-[f,ij]isoquinoline-2,7-dione compounds were disclosed which overcome many of the disadvantages of cobalt acetate as a toner for polyesters while also being stable under the conditions of polymerization and melt processing. These compounds are also stable to light and to other environmental conditions to which fibers and plastics may be exposed and do not deleteriously affect the overall physical properties of the fibers or plastics.

These compounds correspond to the following structure formula I:

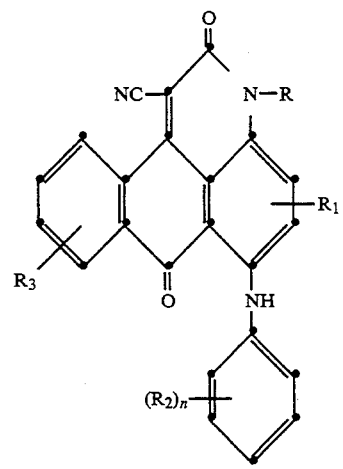

wherein
R is hydrogen, cycloalkyl, allyl, alkyl, aralkyl, alkoxyalkyl or cycloalkylalkylene;

$R_1$ is hydrogen, halogen, alkyl, alkoxy, aryloxy, alkylthio, or arylthio;

$R_2$ is hydrogen, alkyl, aryl, alkoxy, arylalkoxy, alkylthio, arylthio, carbalkoxy, carbaralkoxy, carboxy, sulfamoyl, alkylsulfamoyl, dialkylsulfamoyl, alkylarylsulfamoyl, cycloalkylsulfamoyl, arylsulfamoyl, carbamoyl, alkylcarbamoyl, dialkylcarbamoyl, alkylarylcarbamoyl, cycloalkylcarbamoyl, arylcarbamoyl, 2-pyrrolidono, acylamido or N-alkylacylamido;

$R_3$ is one or more residues selected from the group consisting of hydrogen, halogen, alkyl and alkoxy; and n is an integer of 1 to 5;

wherein one or more alkyl, alkoxy, aryl, aryloxy, alkylthio, arylthio or aralkyl groups may contain one or more reactive residues selected from the group consisting of carboxy, carbalkoxy, carbaryloxy, N-alkylcarbamoyloxy, carbamoyloxy, acyloxy, chlorocarbonyl, hydroxyl, cycloalkylcarbonyloxy, N-arylcarbamoyloxy and N,N-dialkylcarbamoyloxy, wherein said alkyl and aryl groups may further contain substituents such as alkoxy, acyloxy, halogen, cyano, hydroxy and acylamido.

The disclosed process for preparing compounds of formula (I) consisted of reacting an intermediate 1-amino-4-haloanthraquinone (II) with chloroacetyl chloride or chloroacetic anhydride to give 1-(chloroacetamido-4-halogenoanthraquinones (III), which were then

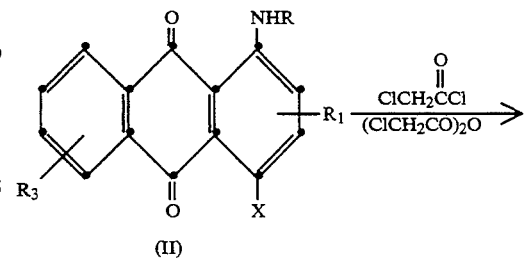

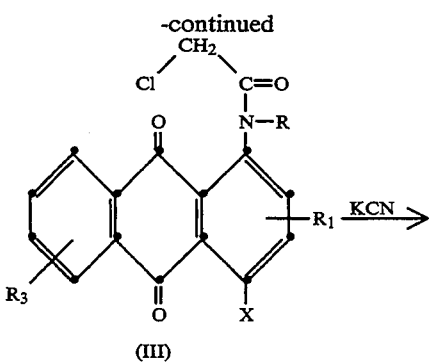

(III)

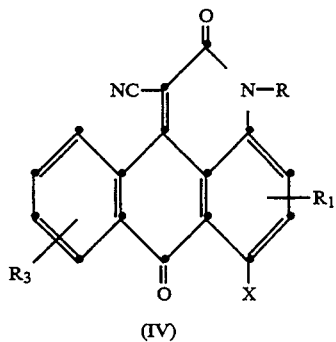

(IV)

treated with an alkali metal cyanide such as potassium cyanide or sodium cyanide (see also, Allen, C. F. H, et al., JACS (January, 1950), 585–88) to give the 1-cyano-6-halogeno-3H-dibenz[f,ij] isoquinoline -2,7-dione intermediate (IV), which was reacted with anilines by a modified Ullman reaction involving nitrogen arylation of said anilines in the presence of copper catalysts as shown below:

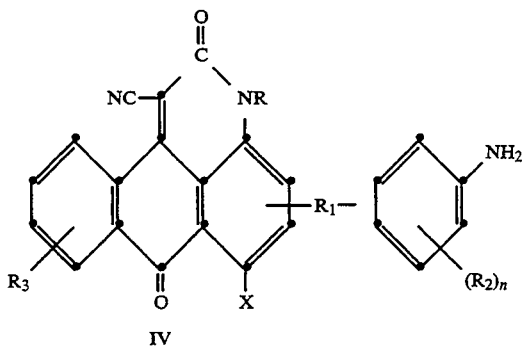

IV

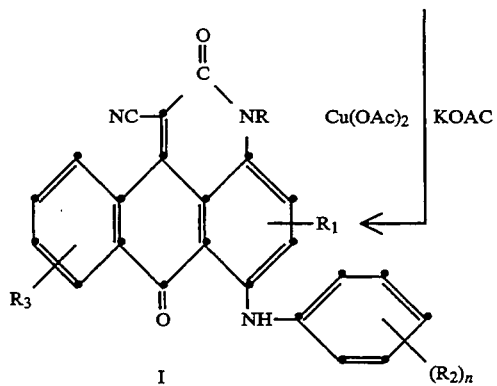

I to give desired compounds of formula (I).

Recent experience has shown the presently known process described above to present many difficulties and problems, including low yields, poor quality, toxicity and safety hazards, environmental concerns over the disposal of reaction by-products, and consequent poor economic yield. First, the use of chloroacetyl chloride or chloroacetic anhydride presents difficulties with regard to safety because of their lachrymatory and toxiological properties. Also, the conversion of (III) into (IV) requires the use of sodium cyanide or potassium cyanide and is very solvent dependent, with the only two known useful solvents being acetonitrile or 2-hydroxyethyl acetate. Acetonitrile is very toxic and volatile and disposal of the acetonitrile/cyanide wastes creates major environmental problems. Another potential solvent, 2-hydroxyethyl acetate, is expensive and the handling and disposal thereof present toxicological and environmental concerns as well. Of even more critical concern are the low yields and poor quality of intermediate compounds (IV) and the blue toners (I) prepared therefrom, which must be repeatedly recrystallized from hazardous high boiling solvents such as nitrobenzene to remove undesirable impurities thereby resulting in a very low yield of usable blue toners (I) (see U.S. Pat. No. 4,745,174 and Comparative Example 3 herein). It has also been found that the quality and purity of toners (I) vary greatly giving blue toners which are not consistent in their degree of redness or greenness in color, thus seriously limiting their effectiveness as toners.

SUMMARY OF THE INVENTION

The present invention provides an improved process for the manufacture of blue toners (I) as defined above. Advantages of the new process include quality, yield, economics and fewer safety/environmental concerns. It is particularly noted that the final toner products can be produced in relatively high yields and with consistent color, starting with readily available 1-amino-4-halogenoanthraquinones.

DETAILED DESCRIPTION OF THE INVENTION

The present invention provides a process for preparing a compound of formula (I) as defined above which comprises the steps (a) reacting a compound of the formula

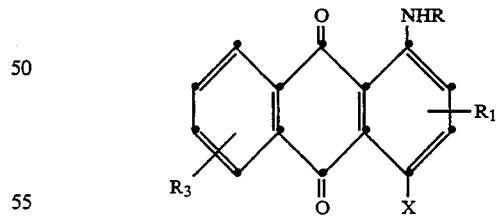

wherein R, $R_1$, and $R_3$ are as defined above; wherein X is chloro, bromo, or iodo, with a compound of the formula

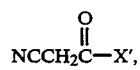

wherein X' is halo; or reaction with an in situ reactant formed from the reaction of cyanoacetic acid with phosphorus oxychloride; to form a compound of the formula

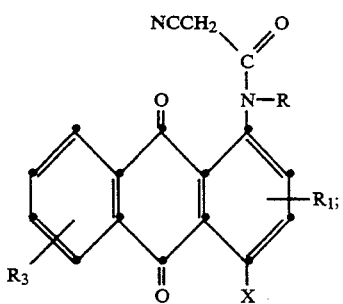

followed by
(b) treatment with a base to provide a compound of the formula

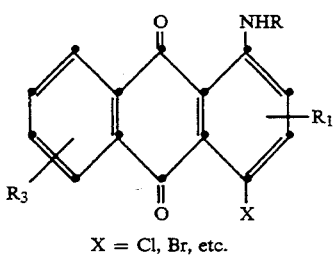

followed by
(c) reaction with a compound of the formula

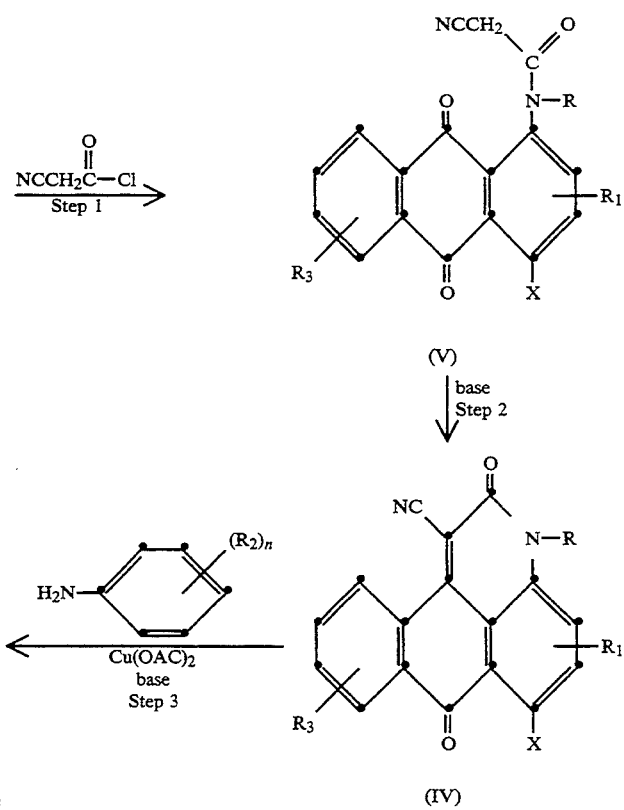

in the presence of a copper salt and a base.

In the above process, the term halo is intended to have its ordinary meaning. In other words, this term is intended to denote groups such as choro, bromo, and iodo. The term "alkyl" is intended to denote a straight or branched-chain $C_1$–$C_{12}$ alkyl group and "acyl" is intended to denote a $C_1$–$C_{12}$ alkyl—C(O)—O— group.

As a further aspect of the present invention, there is provided the first two steps of the above process for preparing the penultimate compound.

A preferred aspect of the process of the present invention may be outlined as follows:

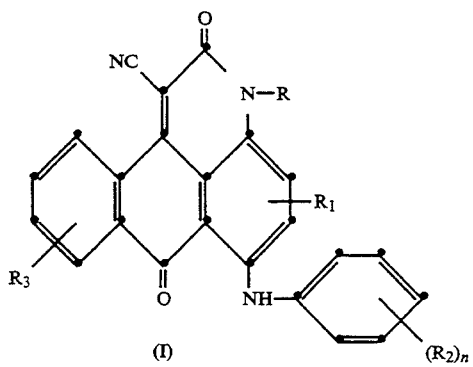

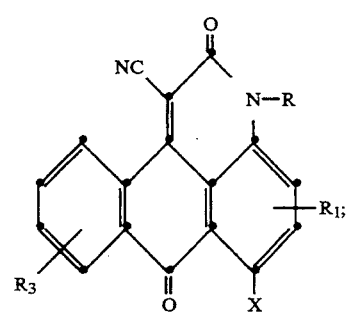

In this process the starting 1-amino-4-halogenoanthraquinones (II) can be reacted with a cyanoacetyl halide, preferably cyanoacetyl chloride, advantageously prepared from readily available cyanoacetic acid and reacted in situ, to give intermediates (V) in high yields, which produce high yields of desired intermediates (IV) upon ring closure under relatively mild conditions in the presence of bases. Compounds (IV) thus produced are of high purity and are useful in producing high quality toners (I) without subsequent purification steps. The overall yield of blue toners (I), based on the starting 1-amino-4-halogenoanthraquinone, is significantly increased by using the improved process of this invention versus the known process. Further, the materials are consistently of higher quality including shade or color, which make them particularly effective as toners, because the degree of redness and greenness is so highly reproducible.

In a preferred embodiment, Step 1 is carried out in readily available and nontoxic aliphatic esters containing 3–5 carbons, such as methyl acetate, ethyl acetate, methyl propionate, ethyl propionate, isopropyl acetate, butyl acetate, methyl isobutyrate, etc., or mixtures thereof, with ethyl acetate being particularly preferred as well as inert aromatic hydrocarbons such as xylenes, toluene, benzene, etc. It is also preferred that the reactant used in Step 1 be prepared in situ using cyanoacetic acid and phosphorous oxychloride. The preferred temperature range is from about 60° C. to about 100° C. Step 2 is preferably accomplished using an aprotic polar solvent such as N,N-dimethylformamide, N,N-dimethylacetamide, N-methyl-2-pyrrolidinone and hexamethylphosphortriamide or mixtures thereof or with an aliphatic ester as described above, with N,N-dimethylformamide being especially preferred. Organic bases are particularly effective in accomplishing the ring closure of Step 2 and may be selected from dialkylamines, trialkylamines, pyridine, picolines, quinoline, isoquinoline, morpholine, piperidine, etc., with pyridine being especially preferred, as well as alkali metal carbonates, e.g., potassium carbonate and sodium carbonate. The ring closure can be accomplished over a fairly wide temperature range, but a temperature of about 10° C. to about 100° C. is generally preferred. Reaction of the intermediate 1-cyano-6-halogeno-3H-dibenz[f,ij]isoquinoline-2,7-diones thus prepared with the aromatic amine(s) (Step 3) is preferably accomplished by using the aprotic solvent(s) or the inert aromatic solvents mentioned in Step 2 as solvents with bases such as alkali metal carbonates or acetates present, with potassium carbonate being especially preferred. The reactions are usually carried out over a temperature range of about 70° C. to about 120° C., with about 90° C. to about 110° C. being especially preferred.

The compounds prepared by the process of this invention are useful as colorants for polyester fibers, films and plastics and may be applied as textile dyes or admixed by melt blending, dry blending or solvent blending followed by high temperature extrusion. They also may be added at various stages during the polymerization process and when the compounds have polyester reactive groups, for example hydroxy, carboxy or carboxylic acid esters, the colorants may be incorporated into the polymer itself. A particularly useful property of the compounds is their ability to serve as toners to impart whiteness to polyester fibers and neutrality of color to polyester films and plastics.

Particularly preferred compounds are those of the formula

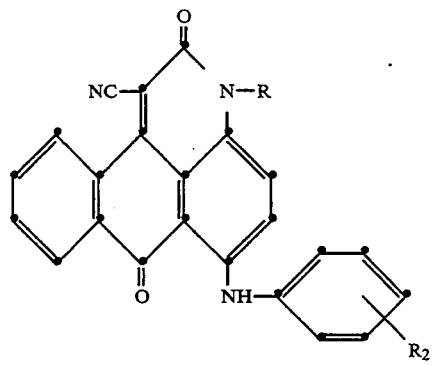

wherein R is $C_1$–$C_6$-straight or branched chain alkyl, cycloalkyl, and $C_1$–$C_6$ straight or branched chain alkyl substituted with hydroxy or $C_1$–$C_4$ alkanoyloxy;

$R_2$ is hydrogen, $C_1$–$C_4$ alkyl, $C_1$–$C_4$ alkoxy, $C_1$–$C_4$ alkyl substituted with hydroxy or $C_1$–$C_4$-alkanoyloxy and $C_1$–$C_4$-alkoxy substituted with hydroxy or $C_1$–$C_4$-alkanoyloxy; with the provision that at least one hydroxy or $C_1$–$C_4$-alkanoyloxy group be present to allow incorporation of the toner in the structure of the polyester molecule when added during the polymerization process. As a preferred embodiment of the process, the methods, and the composition of the present invention, the blue toners have the foregoing structure.

When the toner molecule has one esterification reactive group or a functionality of one, the toner molecule will function as a chain terminating group when added to the polyester polymerization reaction and is incorporated in the polyester structure as a terminal group on the polyester molecule.

In each instance, the toner molecule is bonded to the polymer molecule through the primary valence forces of an ester bond.

Where the toners do not contain an esterifiable reactive group, they may be incorporated into the polyester by mixing either during the course of the polymerization reaction by melt or solution mixing with the polyester using conventional apparatus such as a two roll mill, or by mixing with molten polyester during fiber spinning operations.

As a further aspect of the present invention, there is provided a method for imparting improved whiteness or neutrality of color to polyester fibers and plastics which comprises of adding one or more of the above compounds, prepared by the process of this invention, in combination with small quantities of one or more thermally stable red component(s) to the polymer either before, during or after the polyester forming condensation reaction, said red component being selected from the following structures:

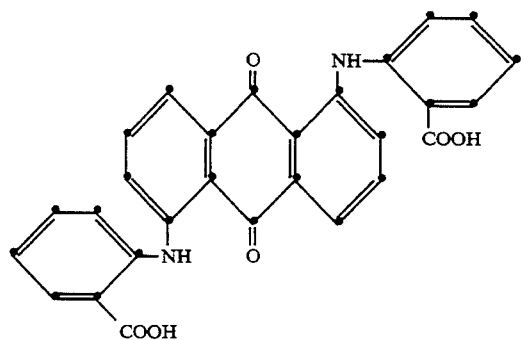
Disclosed in
U.S. 3,459,570
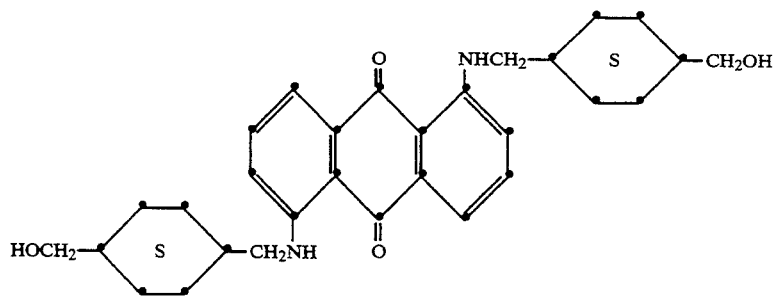
Disclosed in
U.S. 4,420,581,
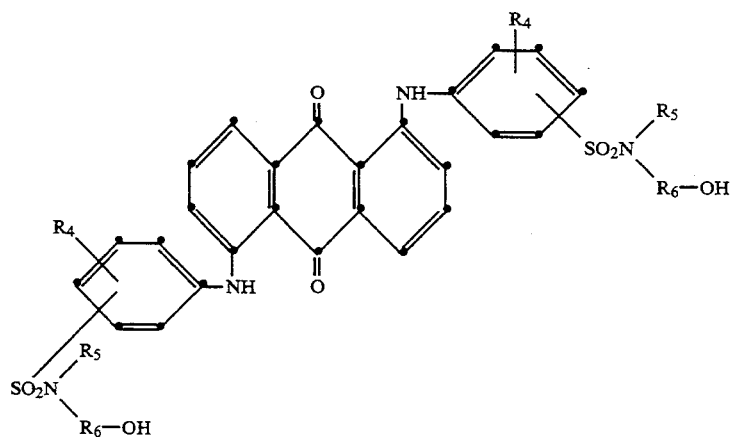
Disclosed in
U.S. 4,403,092,
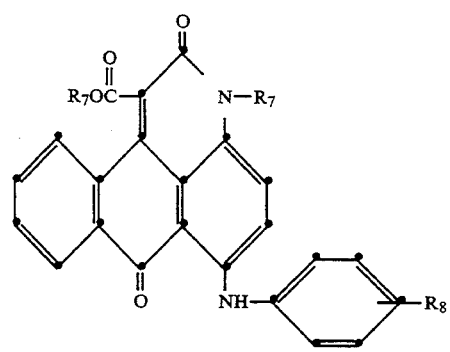
Disclosed in
U.S. 4,790,581 and

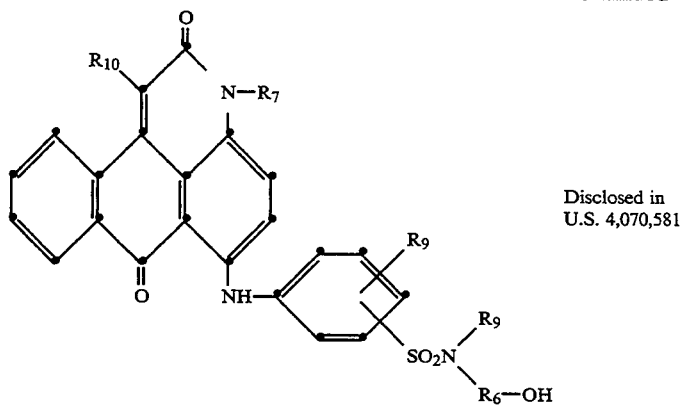

Disclosed in
U.S. 4,070,581

-continued wherein $R_4$ is hydrogen, $C_1$-$C_4$-alkyl or $C_1$-$C_4$-alkoxy; $R_5$ is hydrogen, $C_1$-$C_4$ alkyl or $C_1$-$C_4$ alkyl substituted with hydroxy; $R_6$ is $C_2$-$C_6$-alkylene; $R_7$ is $C_1$-$C_4$-alkyl; $R_8$ is selected from hydrogen, halogen, $C_1$-$C_4$-alkyl or $C_1$-$C_4$-alkoxy; $R_9$ is hydrogen, $C_1$-$C_4$-alkyl or $C_1$-$C_4$-alkoxy; $R_{10}$ is hydrogen or carb-$C_1$-$C_4$-alkoxy. The especially preferred red component is 1,5-di(o-carboxyanilino)anthraquinone. As noted above, these compounds are described in U.S. Pat. Nos. 4,359,570; 4,420,581; 4,403,092; 4,790,581; and 4,070,581, incorporated herein by reference.

It is preferred that the red compounds have a visible absorption maximum in the range of about 520 nm to about 530 nm when the visible absorption spectrum is run in methylene chloride or N,N-dimethylformamide.

Normally less than 10 parts per million of the blue toner and red component combined based on the weight of the polyester is added, with the optimum toning effect being achieved by adding from about 1 to about 6 parts per million of the combined blue toner and red component. The degree redness or greenness desired is usually achieved by varying the ratio of blue toner to red component from abut 14:1 to about 3:1.

This method for imparting whiteness or neutrality of color by compensating for the undesirable yellow color inherently produced under normal polyester manufacturing by addition of the pure blue toners proposed by the process of this invention in combination with a red component gives a much greater flexibility in degree of redness and greenness achieved and gives more reproducible results than the use of the single component toner taught in the prior art.

Suitable polyesters of this invention are those having recurring units of the formula

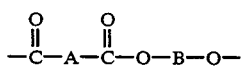

wherein A is selected from the group consisting of

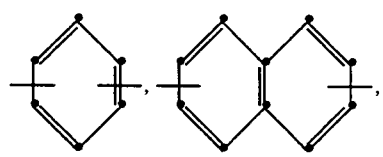

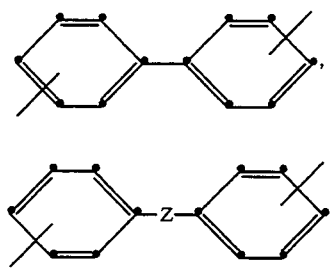

and branched or linear alkylene radicals containing from 2-10 carbon atoms, where Z is selected from the group consisting of branched or linear ($C_1$-$C_4$) alkylenes, —O—, —S—, and —$SO_2$—.

Typical radicals include those derived from terephthalic acid, isophtahlic acid, p,p'-dicarboxydiphenylmethane, and aliphatic, cycloaliphatic and aryl esters and half esters thereof, ammonia and amine salts thereof, and acid halides thereof and the like. Examples of such alkylene radicals are those derived from succinic and adipic acid.

B is a divalent radical selected from the group consisting of branched or linear ($C_2$-$C_{10}$) alkylenes and ($C_5$-$C_{10}$) cycloalkylenes such as radicals derived from a glycol of the series $HO(CH_2)_nOH$, wherein n is an integer from 2 to 10, or cycloaliphatic glycols.

Polyesters of the present invention are prepared by either batch or continuous processes. The polyesters may be prepared by reaction between dihydric alcohols and dibasic acids, esters, acid chlorides or anhydrides. Typically, a dibasic acid ester is prepared from a dibasic acid and a volatile alcohol.

Normally the polyesters are prepared by reacting one or more such dibasic acids or esters with an excess of one or more dihydric alcohols in the presence of a suitable catalyst under reduced pressure.

Among the polyesters and copolyesters useful in the instant invention are those resulting from reacting one or more of the glycols of the series $HO(CH_2)_nOH$, wherein n is an integer from 2 to 10, cycloaliphatic glycols with one or more dicarboxylic acids, or ester forming derivatives thereof.

Among the dicarboxylic acids and ester forming derivatives thereof which are useful in the present invention, there may be named terephthalic acid, isophthalic acid, 2,6-naphthalenedicarboxylic acid, p,p'-dicarboxydiphenyl, p,p'-dicarboxydiphenylsulphone, p,p'-dicarboxyldiphenylmethane, 1,4-cyclohexanedicarboxylic acid, 1,3-cyclohexanedicarboxylic acid, succinic acid, glutaric acid, adipic acid, 1,12-dodecanedioic acid and aliphatic and aryl esters, half esters and acid halides of the above named compounds.

Examples of the polyhydric alcohols which may be employed in practicing the instant invention are ethylene glycol, 1,4-cyclohexanedimethanol, 1,2-propanediol, 1,3-propanediol, 1,4-butanediol, 2,2-dimethyl-1,3-propanediol, 1,6-hexanediol, 1,2-cyclohexanediol, 1,4-cyclohexanediol, 1,2-cyclohexanedimethanol, diethylene glycol, triethylene glycol, dipropylene glycol or tripropylene glycol, and x,8-bis(hydroxymethyl)tricyclo[5,2,1.0]-decane wherein a represents 3, 4 or 5.

The preferred polyesters of the present invention acid moiety comprises at least 50 mole percent of the residue of terephthalic acid and a diol moiety comprising ethylene glycol or at least 50 mole percent of a mixture of ethylene glycol and 1,4-cyclohexanedimethanol.

Another preferred polyester of the instant invention is one wherein the polyester comprises a polyester of a diol comprising 1,4-cyclohexanedimethanol and a dibasic acid comprising terephthalic acid or ester thereof. Yet another preferred polyester is one wherein the diol includes up to 50 mole percent of ethylene glycol.

More preferred polyesters of the present invention are linear polymers exhibiting thermoplastic characteristics and, in general, have an inherent viscosity (I.V.) of about 0.4 to about 1.2 deciliters per gram.

A preferred method for preparing polyesters incorporating toners of the instant invention is by ester interchange. This is the exchange of an ester such as dimethylterephthalate. One or more glycols such as ethylene glycol, suitable catalysts and less than 10 parts per million of blue/red toner are changed to a reactor and heated at about 200° C. and 225° C. under a nitrogen atmosphere.

This first stage of the reaction produces the bisglycolate of the dibasic acid which, without further separation, is employed in the second stage to produce the polyester.

After the ester interchange reaction, a catalyst-inhibitor such as a phosphate ester is added to the reaction product and the reaction product is polycondensed. The preferred phosphate ester has the formula

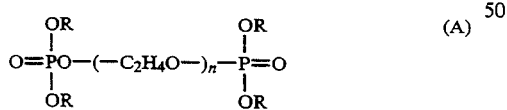

wherein n has an average value of 1.5 to about 3.0, with about 1.8 being most preferred; and each R is hydrogen or an alkyl radical having from 6 to 10 carbon atoms, with octyl being most preferred, the ratio of the number of R groups of hydrogen atoms to the number of phosphorus atoms being about 0.25 to 0.50, with about 0.35 being most preferred and the ester having a free acidity equivalent of about 0.2 to 0.5.

The ester is present in an amount to provide 13–240 parts of phosphorus per million based on the acid fraction of the polyester to be produced.

Other phosphate esters useful in this context include ethyl acid phosphate, diethyl acid phosphate, triethyl acid phosphate, arylalkyl phosphates, tris-2-ethylhexyl phosphate and the like. Preferred phosphate esters are those described in U.S. Pat. No. 3,962,189, incorporated herein by reference.

In the second stage, the reaction is preferably conducted at a sufficiently reduced pressure so as to allow polycondensation to take place at the reaction temperature employed. Reduced pressure is utilized to remove the free polyhydric alcohol which is volatilized under these conditions and removed from the system.

The polyester resulting from the polymerization process of this invention is water clear with a desirable, very slight blue tint as compared to a polyester prepared without a blue toner which exhibits an undesirable yellow color.

Thus, as a further aspect of the present invention, there is provided a polyester composition having admixed or copolymerized therein a compound of the formula

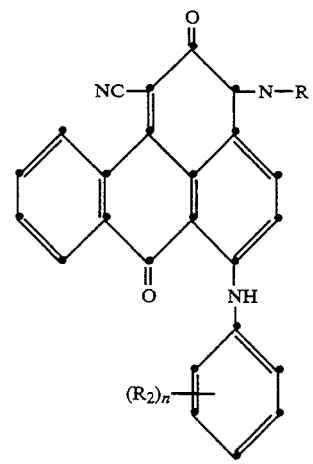

wherein

R is hydrogen, cycloalkyl, allyl, alkyl, aralkyl, alkoxyalkyl or cycloalkylalkylene;

$R_2$ is hydrogen, alkyl, aryl, alkoxy, arylalkoxy, alkylthio, arylthio, carbalkoxy, carbaralkoxy, carboxy, sulfamoyl, alkylsulfamoyl, dialkylsulfamoyl, alkylarylsulfamoyl, cycloalkylsulfamoyl, arylsulfamoyl, carbamoyl, alkylcarbamoyl, dialkylcarbamoyl, alkylarylcarbamoyl, cycloalkylcarbamoyl, arylcarbamoyl, 2-pyrrolidono, acylamido or N-alkylacylamido; and n is an integer of 1 to 5;

wherein one or more of said alkyl, alkoxy, aryl, aryloxy, alkylthio, arylthio or aralkyl groups contain one or more reactive groups selected from the group consisting of carboxy, carbalkoxy, carbaryloxy, N-alkylcarbamoyloxy, carbamoyloxy, acyloxy, chlorocarbonyl, hydroxyl, cycloalkylcarbonyloxy, N-arylcarbamoyloxy and N,N-dialkylcarbamoyloxy, wherein said alkyl and aryl groups may further contain one or more alkoxy, acyloxy, halo, cyano, hydroxy, and arylamido groups;

in a concentration of about 1 to about 10 parts per million, along with one or more compounds selected from the group consisting of

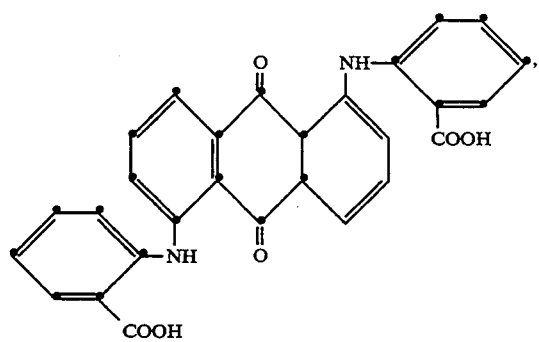
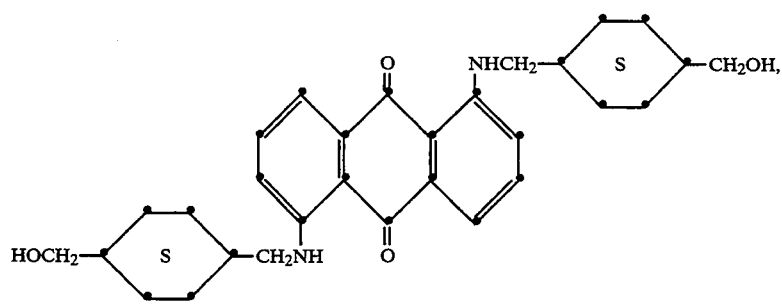
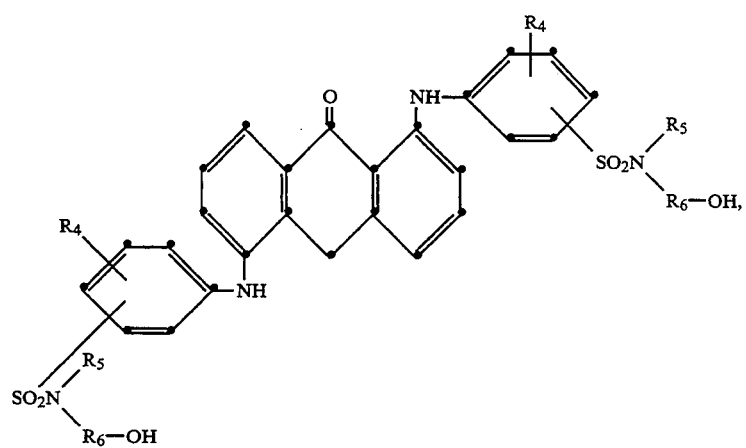
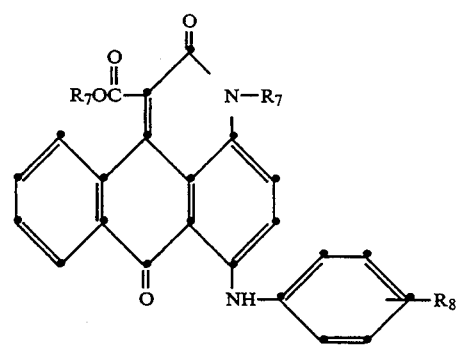

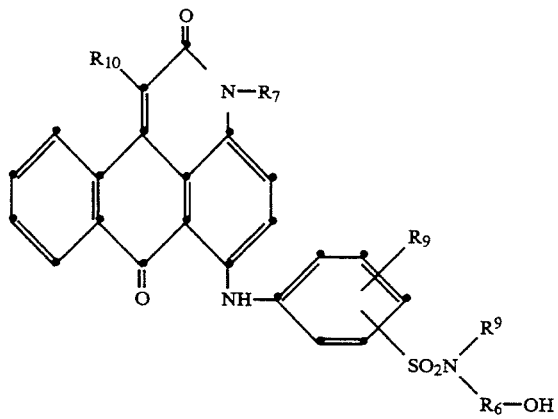

wherein $R_4$ is hydrogen, $C_1$-$C_4$-alkyl or $C_1$-$C_4$-alkoxy; $R_5$ is hydrogen, $C_1$-$C_4$ alkyl or $C_1$-$C_4$ alkyl substituted with hydroxy; $R_6$ is $C_2$-$C_6$-alkylene; $R_7$ is $C_1$-$C_4$-alkyl; $R_8$ is selected from hydrogen, halogen, $C_1$-$C_4$-alkyl or $C_1$-$C_4$-alkoxy; $R_9$ is hydrogen, $C_1$-$C_4$-alkyl or $C_1$-$C_4$-alkoxy; and $R_{10}$ is hydrogen or carb-$C_1$-$C_4$-alkoxy; in a concentration of about 1 to 3 parts per million.

The following examples are included to serve to further illustrate the invention. It will be understood that the examples given are by way of exemplification only and are not to be considered as limiting the scope of the invention.

EXPERIMENTAL SECTION

EXAMPLE 1

To ethyl acetate (1500 ml) was added dry 1-methylamino-4-bromoanthraquinone (158.08 g, 0.50 m) with stirring. Cyanoacetic acid (85.06 g, 1.00 m) was added and the mixture heated at reflux while approximately 100 milliliters of distillate were collected. The temperature was allowed to drop somewhat and phosphorous oxychloride (153.3 g, 1.00 mole) was added dropwise with good stirring and the reaction mixture was refluxed for three hours. Methanol (150 ml) was added gradually and refluxing continued for about 1.0 hour after complete addition. After allowing to cool to room temperature the reaction mixture was filtered and the product washed well with ethanol and dried to give 185.87 g of product (97.0% of the theoretical yield - assuming 100% assay). Liquid chromatography showed the product to consist mostly of 4-bromo-N-[(α-cyanoacetyl)-N-methylamino]-anthraquinone.

EXAMPLE 2

A portion (28.74 g, 0.075 m) of the product from Example 1 was added to N,N-dimethylformamide with stirring. Pyridine (14.0 ml) was added and the reaction mixture was heated and stirred at about 80° C. for one hour. After cooling slowly to room temperature the reaction mixture was filtered and the product washed with N,N-dimethylformamide (25 ml), then washed with ethanol and dried in air. The yield of product was 24.10 g (88% weight yield) which showed an assay of 95.97% by high pressure liquid chromatography for the desired 6-bromo-1-cyano-3-methyl-3H-dibenz[f,ij]isoquinoline-2,7-dione, giving an assay yield of 84.4% of the desired anthrapyridone compound. The percent assay yield of product, based on the two steps, starting with 1-methylamino-4-bromoanthraquinone, was 0.97×0.844×100 or 81.9%.

EXAMPLE 3

A sample of 6-bromo-1-cyano-3-methyl-3H-dibenz[f,ij]isoquinoline-2,7-dione (36.5 g of 96% assay material - 35.0 g pure material, 0.10 m) prepared is in Example 2, p-aminophenylethanol (55.0 g), potassium carbonate (10.0 g), cupric acetate (12.0 g) and N,N-dimethylformamide (100 ml) were mixed and heated at about 70° C. for 1 hr. The temperature was then increased to about 80° C. and held for 1 hr, increased to about 90° C. and held for 1 hr, increased to about 100° C. and held for 1 hr and finally increased to 110° C. and held for 2 hrs. Additional N,N-dimethylformamide (140 ml) and isopropanol (280 ml) were added at about 80° C. and the reaction mixture allowed to cool to room temperature. The product was collected by filtration, washed with isopropanol, water and again with isopropanol. After drying the product weighed 34.97 g (85.5% weight yield) and was determined to have an assay of 95.2% by high pressure liquid chromatography to give an assay yield of 0.952×0.855×100 or 81.3% of 1-cyano-6-[4-(2-hydroxyethyl)anilino]-3-methyl-3H-dibenz[f,ij]isoquinoline-2,7-dione. The product as produced was very pure and did not require further purification by recrystallization. The overall percent assay yield for the three steps, based on starting with 1-methylamino-4-bromoanthraquinone, was 0.97×0.844×0.813×100 or 66.6%.

COMPARATIVE EXAMPLE 1

A mixture of 1-methylamino-4-bromoanthraquinone (63.2 g, 0.20 m) and ethyl acetate (600 ml) was heated and any low boiling material removed until a constant boiling point for ethyl acetate was achieved. Chloroacetyl chloride (34.0 g, 0.30 m) was added under the surface and stirring continued at reflux for 0.5 hr. The reaction mixture was cooled to about 55° C. and methanol (300 ml) was added, followed by cooling to 0.50° C. The product was collected by vacuum filtration, washed with methanol (400 ml) and dried in air. The yield of 1-N[(α-chloroacetyl)-N-methylamino]-4-bromoanthraquinone was 60 g (76.4% of the theoretical by weight). The product had an assay of 96.0% by high pressure liquid chromatography thus giving an assay yield of 0.76×0.960×100 or 73.0%, based on the starting 1-methylamino-4-bromoanthraquinone.

COMPARATIVE EXAMPLE 2

A portion of the product from Comparative Example 1 (44.25 g of 96.0% assay material - 43.48 g pure material, 0.108 m) and acetonitrile (314.5 g) were mixed and heated to reflux with stirring. A solution of potassium cyanide (3.25 g) dissolved in water (5 ml) was added dropwise over 15 minutes with stirring and refluxing continued for 1 hr. Another solution of potassium cyanide (8.35 g) dissolved in water (12.0 ml) was added dropwise over 30 minutes and refluxing continued for 2 hrs. Methanol (237 ml) was added at about 40° C. The mixture was stirred at about 0°-5° C. for 1 hr. and the product collected by vacuum filtration, washed with methanol 980 ml) and dried. The product weighed 25.0 g (65.4% of the theoretical by weight). By high pressure liquid chromatography the product assayed 91.1% as 6-bromo-1-cyano-3-methyl-3H-dibenz[f,ij]isoquinoline-2,7-dione thus giving an assay yield of 0.911×0.654×100 or 59.6%. The percent assay yield of desired product based on the two steps, starting with 1-methylamino-4-bromoanthraquinone, was 0.730×0.596×100 or 43.5%. This compared with an assay yield of 81.9% for the two steps of Examples 1 and 2 above when the process of the invention was used.

COMPARATIVE EXAMPLE 3

A sample of 6-bromo-1-cyano-3-methyl-3H-dibenz[-f,ij]isoquinoline-2,7-dione (21.92 g of 91.1% assay material - 19.97 g of pure material, 0.0565 m) as prepared in Comparative Example 2, p-aminophenylethanol (108.0 g), potassium acetate (28.8 g), cupric acetate (7.2 g) and N,N-dimethylformamide (84.6 g) were mixed and heated with stirring at 110°-115° C. for 2 hrs. The mixture was cooled to 65° and methanol (190 g) was added and refluxing continued for 1 hr. After cooling to about 20°-25° C., the reaction mixture was filtered and the product washed with methanol (285 g), followed by water (1,800 ml) and then methanol (143 g). After drying, the product 1-cyano-6-[4-(2-hydroxyethyl)anilino]-3-methyl-3H-dibenz[f,ij]isoquinoline-2,7-dione weighed 12.0 g (51.8% of the theoretical yield by weight and assuming 100% assay). The overall percent assay yield of desired product for the three steps, based on starting with 1-methylamino-4-bromo-anthraquinone, was 0.730×0.596×0.518×100 or 22.5%, which compares with an overall percent assay yield of 66.6%, based on starting with 1-methylamino-4-bromoanthraquinone, according to the process of this invention disclosed in Examples 1, 2 and 3.

EXAMPLE 4 - OLIGOMER PREPARATION

The following reagents were weighed into a three-necked 5000 ml round bottom flask:

| | |
|---|---|
| 1941.9 g | dimethyl terephthalate |
| 1049.0 g | ethylene glycol |
| 447.05 g | 1,4-cyclohexanedimethanol |
| 0.45 g | manganese acetate tetrahydrate (to give 46 ppm Mn/g polymer) |
| 0.99 g | acetyltriisopropyl titanate (to give 56 ppm Ti/g polymer) |

The flask was equipped with an overhead stirrer, thermocouple, and a column (27 inch length, 1.5 inch diameter) packed with glass beads and connected to a water-jacketed take-off condenser. The reaction mixture was heated to a maximum of 240° C. with stirring and the temperature maintained at about 240° C. until methanol ceased evolving. A total of 790 ml of condensate was collected. At this point Merpol A (1.7 g), a mixed phosphorous ester, was added (70 ppm phosphorus/g polymer).

EXAMPLE 4a

A 167 g aliquot (gives 130.5 g of final polymer) of the hot oligomer from Example 4 was transferred into a 500 ml round bottom flask equipped with a nitrogen inlet, stirrer, vacuum outlet and condensing flask. An ethylene glycol solution (~10 ml) containing 3.5 ppm of the blue toner of Example 3 (based on the final weight of the polymer) and 0.25 ppm 1,5-di(carboxyanilino)anthraquinone (based on the final weight of the polymer) was added and the flask then immersed in a molten Belmont metal bath preheated to 275° C.

The temperature was increased to 275° C. with a slow stream of nitrogen bleeding into the system. After stopping the nitrogen flow, a vacuum was applied and the polycondensation completed by heating at less than 1 mm Hg for 45 minutes at 275° C. The flask was removed from the metal bath and allowed to cool in a nitrogen atmosphere. After grinding using a Wiley mill to a particle size of about 6 mm, the inherent viscosity and color were measured. Triplicate runs were made and the results are reported in Table 1.

EXAMPLE 5

Example 4a was repeated exactly except the toner system consisted of 3.5 ppm of the blue toner of Example 3 and 0.29 ppm of 1,5-di-(o-carboxyanilino)anthraquinone. Triplicate runs were made and the results are reported in Table 1.

EXAMPLE 6

Example 4a was repeated exactly except the toner system consisted of 3.5 ppm of the blue toner of Example 3 and 0.35 ppm of 1,5-di-(o-carboxyanilino)anthraquinone. Triplicate runs were made and the results are reported in Table 1.

EXAMPLE 7

Example 4a was repeated exactly except the toner systems consisted of 3.5 ppm of the blue toner of Example 3 and 0.44 ppm of 1,5-di-(o-carboxyanilino)anthraquinone. Triplicate runs were made and the results reported in Table 1.

EXAMPLE 8

Example 4a was repeated exactly except the toner system consisted of 3.5 ppm of the toner of Example 3 and 0.58 ppm of 1,5-di-(o-carboxyanilino)anthraquinone. Triplicate runs were made and the results reported in Table 1.

EXAMPLE 9

Example 4a was repeated exactly except the toner system consisted of 3.5 ppm of the toner of Example 3 and 0.88 ppm of 1,5-di-(o-carboxyanilino)anthraquinone. Triple runs were made and the results reported in Table 1.

COMPARATIVE EXAMPLE 4 - (Control - no toner present)

The following materials were placed in a 500 ml three-necked, round bottom flask:

| | |
|---|---|
| 97.0 g (0.50 m) | dimethyl terephthalate |
| 52.1 g (0.84 m) | ethylene glycol |

-continued

| 23.0 g (0.16 m) | 1,4-cyclohexanedimethanol |
| 0.0050 g | Mn from an ethylene glycol solution of manganese acetate |
| 0.0087 g | Ti from an n-butanol solution of acetyl-triisopropyl titanate |

The flask was equipped with a nitrogen inlet, stirrer, vacuum outlet, and condensing flask. The flask and contents were heated at 200° C. in a Belmont metal bath for 1 hr and at 225° C. for 1 hr with a nitrogen sweep over the reaction mixture. Then 1.05 ml of an ethylene glycol slurry of a mixed phosphorous ester composition (MERPOL A) which contained (0.0087 g phosphorous) was added.

The temperature of the bath was increased to about 280° C. and a vacuum was applied and the polycondensation completed by holding the temperature at about 280°–285° C. for about 50 minutes and the pressure reduced to about 0.3 mm Hg. The flask was removed from the metal bath and was allowed to cool while the polymer crystallized. After grinding using a Wiley mill to a particle size of about 3 mm, the inherent viscosity and color were measured. The results are reported in Table 1.

COMPARATIVE EXAMPLE 5

Example 4a was repeated exactly except the toner consisted of 3.5 ppm of the toner of Comparative Example 3, made by the old process. Duplicate runs were made and the results reported in Table 1.

COMPARATIVE EXAMPLE 6

Example 4a was repeated exactly except the toner consisted of cobalt acetate (75 ppm of cobalt based on the final weight of the polymer). The process was run in duplicate and the results reported in Table 1.

COMPARATIVE EXAMPLE 7

Example 4a was repeated exactly except the toner consisted of 3.5 ppm of the toner of Example 3 with no red component added. Triplicate runs were made and the results reported in Table 1.

All of the results from Examples 4a–9 and Comparative Examples 4–7 are reported in Table 1 and demonstrate the effectiveness of the use of the 1-cyano-6-arylamino-3H-dibenz[f,ij]isoquinoline-2,7-diones prepared by the process of this invention in combination with selected red colorants when used to offset the yellow color of polyesters (a large a* value indicates more-yellow color) and that a good balance of redness and greenness (b*) can be achieved by varying the ratio of the toner to red colorant, giving a very effective method for improving the color of polyester fibers, films and plastics.

The inherent viscosities of the polymers were measured in a 60/40 ratio by weight of phenol/tetrachloroethane at a concentration of 0.5 g per 100 ml.

All color measurements were made on a Hunter Lab color measurement device (Hunter Associates Laboratory) and the CIELAB-L*, a*, b* values measured. The color measurements were made in duplicate or triplicate and averaged.

TABLE I

EFFECT OF TONER ON THE COLOR OF POLYESTER

| Ref. | ppm Blue Toner[1] | ppm Red Colorant | Ratio Blue:Red | IV[3] dL/g | L*[3] | a*[3] | b*[3] |
|---|---|---|---|---|---|---|---|
| Comp. Ex. 4 | NO TONER PRESENT | | — | 0.844 | 80.20 | −2.15 | 13.81 |
| Comp. Ex. 5 | 3.5[1] | 0 | 1:0 | 0.750 (0.04) | 75.44 (1.18) | −2.48 (0.19) | 3.41 (1.38) |
| Comp. Ex. 6 | 75 ppm Cobalt | | — | 0.836 (0.05) | 74.39 (1.15) | −1.16 (0.10) | 6.99 (0.54) |
| Ex. 4a | 3.5[2] | 0.25 | 14:1 | 0.702 (0.03) | 77.78 (0.63) | −2.33 (0.11) | 3.24 (0.56) |
| Ex. 5 | 3.5[2] | 0.29 | 12:1 | 0.732 (0.04) | 75.32 (0.53) | −2.72 (0.06) | 2.08 (0.24) |
| Ex. 6 | 3.5[2] | 0.35 | 10:1 | 0.748 (0.08) | 75.50 (1.98) | −2.38 (0.17) | 2.52 (0.70) |
| Ex. 7 | 3.5[2] | 0.44 | 8:1 | 0.780 (0.06) | 74.16 (1.10) | −2.12 (0.11) | 2.64 (0.79) |
| Ex. 8 | 3.5[2] | 0.58 | 6:1 | 0.777 (0.04) | 75.28 (0.80) | −1.84 (0.18) | 2.55 (0.85) |
| Ex. 9 | 3.5[2] | 0.88 | 4:1 | 0.782 (0.05) | 74.71 (0.50) | −0.89 (0.12) | 3.03 (0.38) |
| Comp. Ex. 7 | 3.5[2] | 0 | 1:0 | 0.776 (0.06) | 75.22 (0.55) | −3.55 (0.11) | 3.54 (0.80) |

[1]Blue Toner prepared by the old process.
[2]Blue Toner prepared by the process of the invention.
[3]Values reported are the average for the different runs: Standard deviations are given in parentheses.

We claim:

1. A method for imparting improved whiteness to a polyester normally appearing yellow, which comprises admixing a blue toner compound of the formula

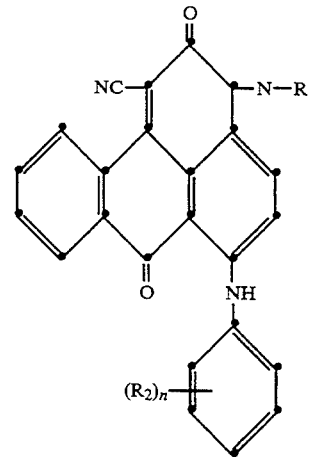

wherein

R is hydrogen, cycloalkyl, allyl, alkyl, aralkyl, alkoxyalkyl or cycloalkylalkylene;

$R_2$ is hydrogen, alkyl, aryl, alkoxy, arylalkoxy, alkylthio, arylthio, carbalkoxy, carbaralkoxy, carboxy, sulfamoyl, alkylsulfamoyl, dialkylsulfamoyl, alkylarylsulfamoyl, cycloalkylsulfamoyl, arylsulfamoyl, carbamoyl, alkylcarbamoyl, dialkylcarbamoyl, alkylarylcarbamoyl, cycloalkylcarbamoyl, arylcarbamoyl, 2-pyrrolidono, acylamido or N-alkylacylamido; and n is an integer of 1 to 5;

wherein one or more of said alkyl, alkoxy, aryl, aryloxy, alkylthio, arylthio or aralkyl groups contain one or more reactive groups selected from the group consisting of carboxy, carbalkoxy, carbaryloxy, N-alkylcarbamoyloxy, carbamoyloxy, acyloxy, chlorocarbonyl, hydroxyl, cycloalkylcarbonyloxy, N-arylcarbamoyloxy and N,N-dialkylcarbamoyloxy, wherein said alkyl and aryl groups may further contain one or more alkoxy, acyloxy, halo, cyano, hydroxy, and arylamido groups;

in a concentration of about 1 to about 10 parts per million, along with one or more red compounds selected from the group consisting of

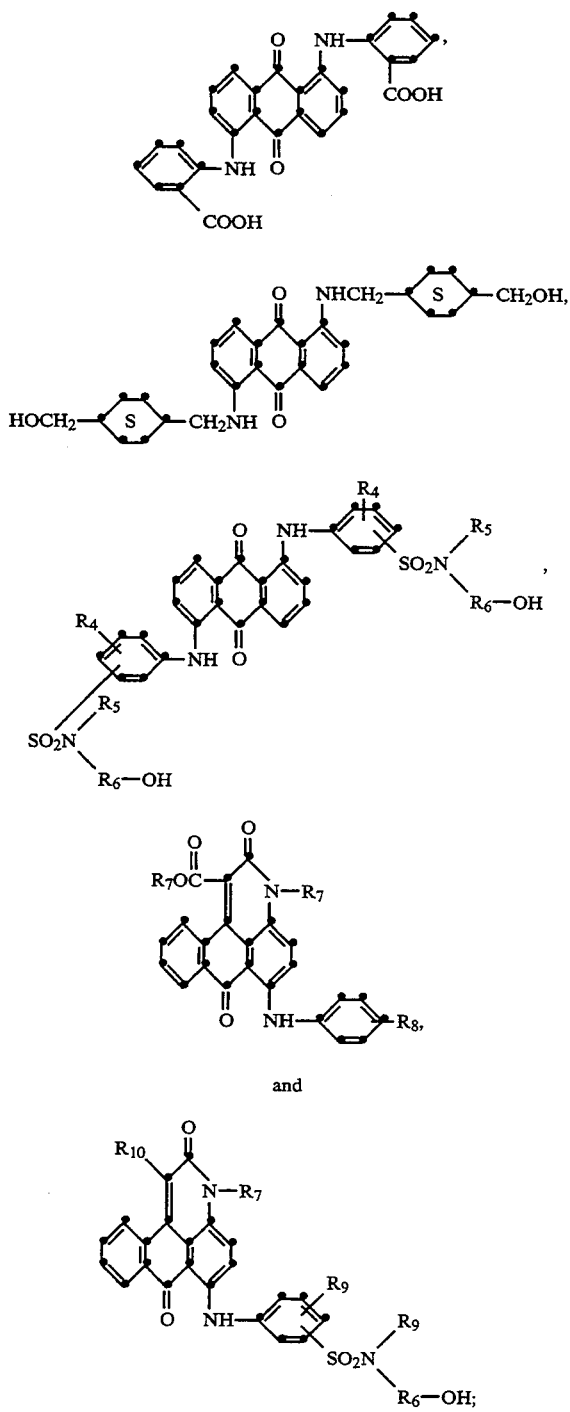

and wherein $R_4$ is hydrogen, $C_1-C_4$-alkyl or $C_1-C_4$-alkoxy; $R_5$ is hydrogen, $C_1-C_4$ alkyl or $C_1-C_4$ alkyl substituted with hydroxy; $R_6$ is $C_2-C_6$-alkylene; $R_7$ is $C_1-C_4$-alkyl; $R_8$ is selected from hydrogen, halogen, $C_1-C_4$-alkyl or $C_1-C_4$-alkoxy; $R_9$ is hydrogen, $C_1-C_4$-alkyl or $C_1-C_4$-alkoxy; and $R_{10}$ is hydrogen or carb-$C_1-C_4$-alkoxy; in a concentration of about 0.1 to 3 parts per million.

2. The method of claim 1, wherein the ratio of blue toner compound to red compound is from about 14:1 to about 3:1.

3. The method of claim 1, wherein the ratio of blue toner compound to red compound is from about 4:1 to 8:1.

4. The method of claim 1, wherein the red compound has the formula

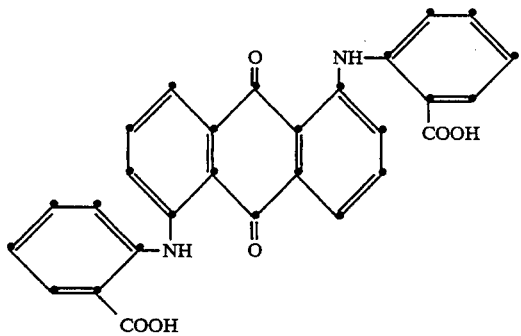

5. The method of claim 1, wherein R is methyl, n is 1, and $R_2$ is 2-(hydroxyethyl) or 2-(hydroxyethoxy).

6. A method for imparting improved whiteness to a polyester normally appearing yellow, which comprises copolymerizing in said polyester a blue toner compound of the formula

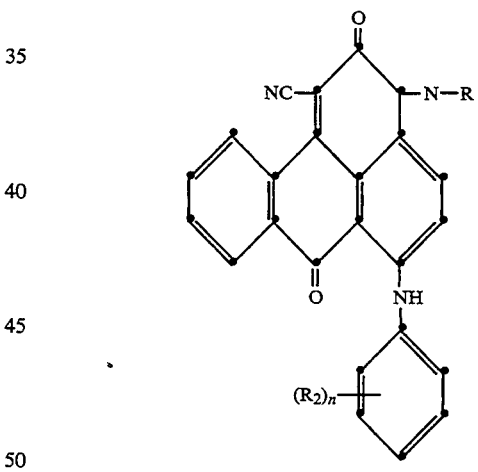

wherein
R is hydrogen, cycloalkyl, allyl, alkyl, aralkyl, alkoxyalkyl or cycloalkylalkylene;
$R_2$ is hydrogen, alkyl, aryl, alkoxy, arylalkoxy, alkylthio, arylthio, carbalkoxy, carbaralkoxy, carboxy, sulfamoyl, alkylsulfamoyl, dialkylsulfamoyl, alkylarylsulfamoyl, cycloalkylsulfamoyl, arylsulfamoyl, carbamoyl, alkylcarbamoyl, dialkylcarbamoyl, alkylarylcarbamoyl, cycloalkylcarbamoyl, arylcarbamoyl, 2-pyrrolidono, acylamido or N-alkylacylamido; and
n is an integer of 1 to 5;
wherein one or more of said alkyl, alkoxy, aryl, aryloxy, alkylthio, arylthio or aralkyl groups optionally contain one or more reactive groups selected from the group consisting of carboxy, carbalkoxy, carbaryloxy, N-alkylcarbamoyloxy, carbamoyloxy, acyloxy, chlorocarbonyl, hydroxyl, cycloalkylcarbonyloxy, N-arylcarbamoyloxy and N,N-dialkylcarbamoyloxy, wherein said alkyl and aryl groups may further contain one or more alkoxy, acyloxy, halo, cyano, hydroxy, and arylamido groups;

in a concentration of about 1 to about 10 parts per million, along with one or more red compounds selected from the group consisting of

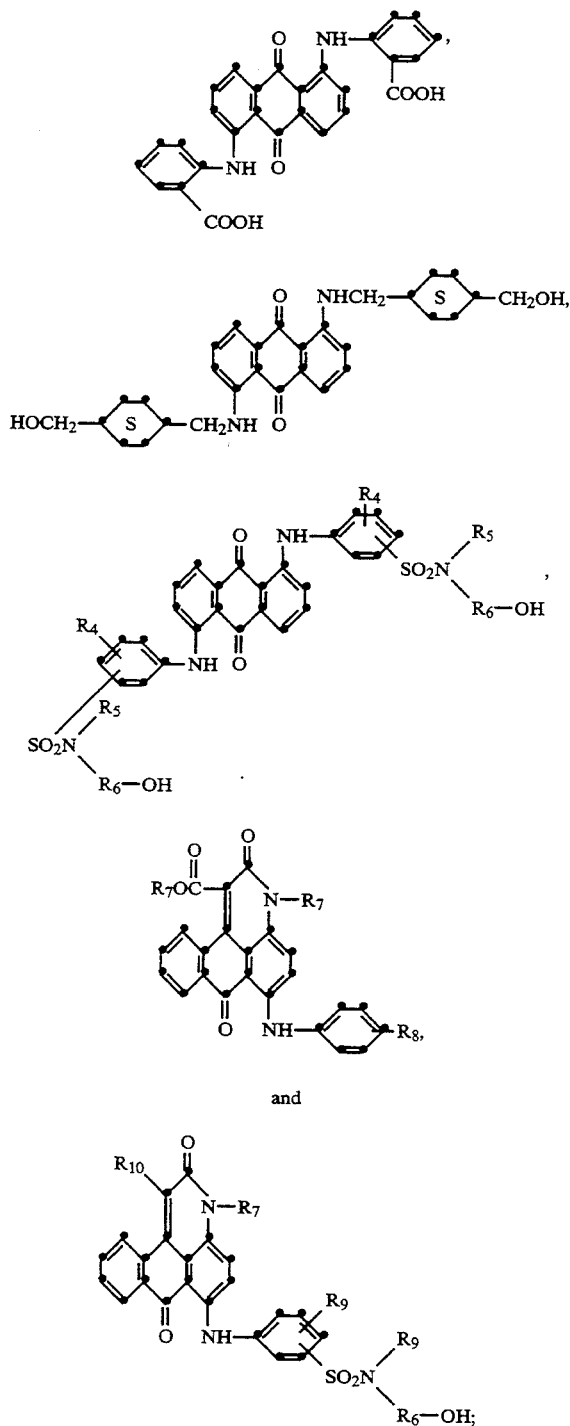

and wherein $R_4$ is hydrogen, $C_1$-$C_4$-alkyl or $C_1$-$C_4$-alkoxy; $R_5$ is hydrogen, $C_1$-$C_4$ alkyl or $C_1$-$C_4$ alkyl substituted with hydroxy; $R_6$ is $C_2$-$C_6$-alkylene; $R_7$ is $C_1$-$C_4$-alkyl; $R_8$ is selected from hydrogen, halogen, $C_1$-$C_4$-alkyl or $C_1$-$C_4$-alkoxy; $R_9$ is hydrogen, $C_1$-$C_4$-alkyl or $C_1$-$C_4$-alkoxy; and $R_{10}$ is hydrogen or carb-$C_1$-$C_4$-alkoxy;

in a concentration of about 0.1 to 3 parts per million.

7. The method of claim 6, wherein the ratio of blue toner compound to red compound is from about 14:1 to about 3:1.

8. The method of claim 6, wherein the ratio of blue toner compound to red compound is from about 4:1 to 8:1.

9. The method of claim 6, wherein the red compound has the formula

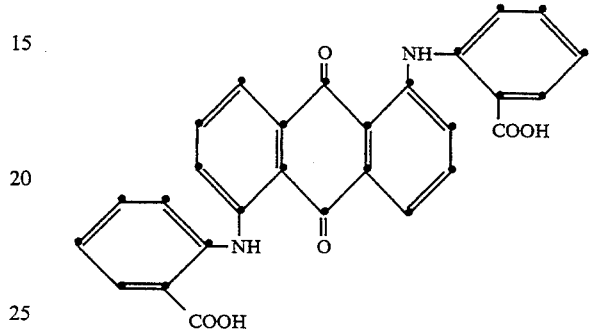

10. The method of claim 6, wherein R is methyl, n is 1, and $R_2$ is 2-(hydroxyethyl) or 2-(hydroxyethoxy).

11. A polyester composition having admixed or copolymerized therein a blue toner compound of the formula

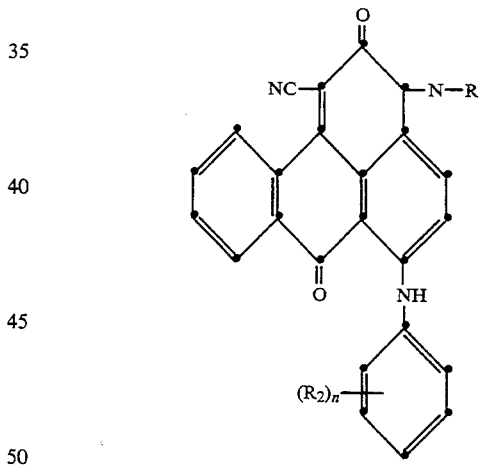

wherein

R is hydrogen, cycloalkyl, allyl, alkyl, aralkyl, alkoxyalkyl or cycloalkylalkylene;

$R_2$ is hydrogen, alkyl, aryl, alkoxy, arylalkoxy, alkylthio, arylthio, carbalkoxy, carbaralkoxy, carboxy, sulfamoyl, alkylsulfamoyl, dialkylsulfamoyl, alkylarylsulfamoyl, cycloalkylsulfamoyl, arylsulfamoyl, carbamoyl, alkylcarbamoyl, dialkylcarbamoyl, alkylarylcarbamoyl, cycloalkylcarbamoyl, arylcarbamoyl, 2-pyrrolidono, acylamido or N-alkylacylamido; and n is an integer of 1 to 5;

wherein one or more of said alkyl, alkoxy, aryl, aryloxy, alkylthio, arylthio or aralkyl groups optionally contain one or more reactive groups selected from the group consisting of carboxy, carbalkoxy, carbaryloxy, N-alkylcarbamoyloxy, carbamoyloxy, acyloxy, chlorocarbonyl, hydroxyl, cycloalkylcarbonyloxy, N-arylcarbamoyloxy and N,N-dialkylcarbamoyloxy, wherein said alkyl and aryl groups may further contain one or more alkoxy, acyloxy, halo, cyano, hydroxy, and arylamido groups;

in a concentration of about 1 to about 10 parts per million, along with one or more red compounds selected from the group consisting of

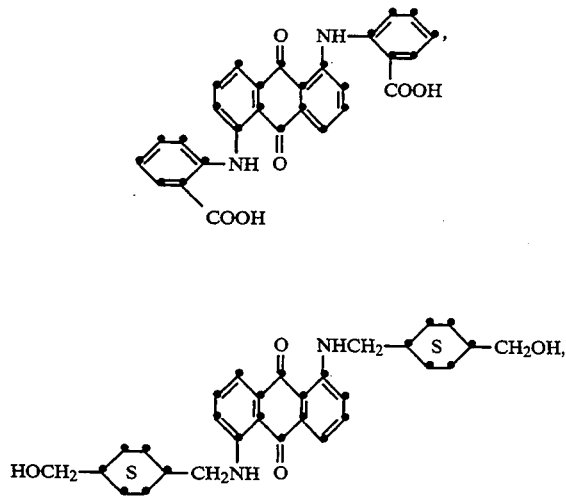

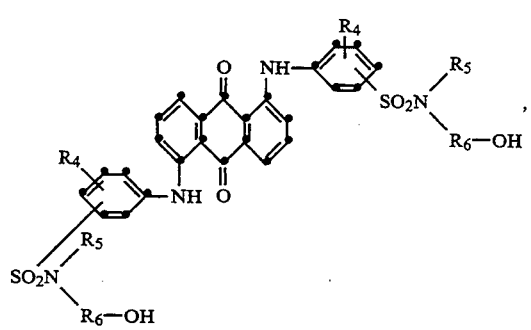

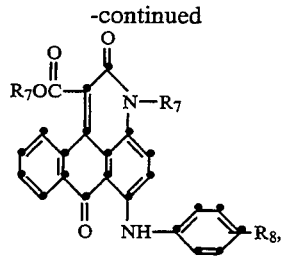

and

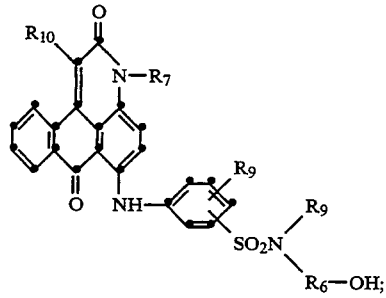

wherein $R_4$ is hydrogen, $C_1$–$C_4$-alkyl or $C_1$–$C_4$-alkoxy; $R_5$ is hydrogen, $C_1$–$C_4$ alkyl or $C_1$–$C_4$ alkyl substituted with hydroxy; $R_6$ is $C_2$–$C_6$-alkylene; $R_7$ is $C_1$–$C_4$-alkyl; $R_8$ is selected from hydrogen, halogen, $C_1$–$C_4$-alkyl or $C_1$–$C_4$-alkoxy; $R_9$ is hydrogen, $C_1$–$C_4$-alkyl or $C_1$–$C_4$-alkoxy; and $R_{10}$ is hydrogen or carb-$C_1$–$C_4$-alkoxy;

in a concentration of about 0.1 to 3 parts per million.

12. The polyester composition of claim 11, wherein the ratio of blue toner compound to red compound is from about 14:1 to about 3:1.

13. The polyester composition of claim 11, wherein the ratio of blue toner compound to red compound is from about 4:1 to 8:1.

14. The polyester composition of claim 11, wherein the red compound has the formula

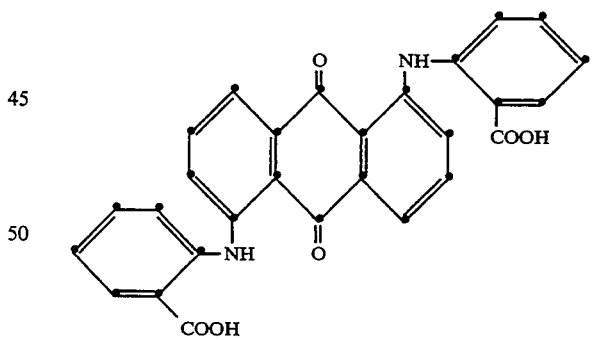

* * * * *